United States Patent [19]

Alenares

[11] 4,085,745
[45] Apr. 25, 1978

[54] ELASTIC SUPPORT FOR THE VEINS OF THE FOOT

[76] Inventor: Santiago S. Alenares, 3038 SW. 8th St., Apt. B202, Miami, Fla. 33135

[21] Appl. No.: 768,598

[22] Filed: Feb. 14, 1977

[51] Int. Cl.² ............................................. A61F 13/00
[52] U.S. Cl. .................................................... 128/165
[58] Field of Search ...................... 128/165, 166, 166.5, 128/156, 167, 80 R; 2/239, 240, 241

[56] References Cited

U.S. PATENT DOCUMENTS

| 982,664 | 1/1911 | Fischer | 128/166.5 |
| 1,220,724 | 3/1917 | Burns | 128/166.5 X |
| 1,365,512 | 1/1921 | Lewis | 128/166.5 |
| 1,406,583 | 2/1922 | Ruge | 128/166.5 |
| 2,281,160 | 4/1942 | Kuerschner | 128/165 X |

FOREIGN PATENT DOCUMENTS

| 1,285,672 | 12/1968 | Germany | 128/166.5 |

*Primary Examiner*—John D. Yasko
*Attorney, Agent, or Firm*—Erwin M. Barnett

[57] ABSTRACT

A vein foot support is made of a two-way stretch elastic material which is shaped to ensure the application of a substantially uniform supportive pressure of predetermined magnitude on the venous system in the tarsal and metatarsal areas including the dorsal venous arch and the medial marginal and lateral marginal veins below the ankle.

4 Claims, 4 Drawing Figures

ELASTIC SUPPORT FOR THE VEINS OF THE FOOT

BACKGROUND OF THE INVENTION

1. Field of the Invention

This invention relates to an elastic foot support and in particular is directed to such supports for preventing and alleviating problems resulting from dilated veins of the foot in the metatarsal and tarsal areas below the ankle.

2. Description of the Prior Art

It appears desirable for persons whose occupations and activities require standing on their feet for relatively long periods of time to protect themselves against the consequences of excessive dilatation of the superficial venous system of the foot. Consequently there is a need for a simple, inexpensive, sanitary and efficient means for affording such protection.

The various prior art arch and ankle supports and braces, being directed to correct conditions and afford protection relative to the muscles, tendons, bones and joints of the foot and ankle, are not adaptable as vein supports. Likewise, elastic stockings and anklets, including those custom-made for therapeutic purposes, have been found to be ineffective in supporting the superficial veins of the foot below the malleoli by failing to apply pressure where needed most and often to aggrevate the condition by applying excessive pressure in the wrong places, for example, around the ankle above the malleoli where the pressure acts as a tourniquet, hampering the upward flow of venous circulation from the foot.

This failure of the various prior art devices is due primarily to the lack of provision for the anatomy of the ankle and the location, with respect to the protruding malleoli, of the large superficial veins of the foot, namely, the medial marginal and the lateral marginal veins which collect the blood from the foot through a collateral network and become the great saphenous and small saphenous veins, respectively, as they emerge above the ankle.

SUMMARY OF THE INVENTION

Among the objects of the invention is to provide a vein foot support constructed to exert a precise and uniform supportive pressure of predetermined magnitude to the superficial veins of the metatarsal and tarsal areas of the foot below the ankle without interference from bony protuberances and anatomical depressions between such protuberances and the anterior and posterior tendons, which vein foot support shall be inexpensive to manufacture by conventional methods from a two-way stretch elastic material either in a variety of sizes or custom-made to individual measurements, which shall be comfortable to wear under regular stockings or socks, be washable and be reliable and efficient in use.

The invention features a supportive structure made of a two-way stretch material, sized and proportioned to extend from a front opening having an elastic border for completely encircling the foot at the base of the toes, along the sole, enclosing the heel and extending upward across the dorsum, that is, the instep, to a top opening also having an elastic border. The latter surrounds the foot just below the ankle, that is, in the rear, the border extends across the lower part of the Achilles tendon, then forwardly on both sides across the medial and lateral aspects just below the lateral malleolus and at the same level on the medial side. The border then curves upwardly across the dorsum, reaching up to but not beyond the angle of the ankle joint. The fit of the vein support on the foot is such that the two-way stretch elastic material is expanded to exert a substantially uniform compressive force of predetermined magnitude. In this regard a uniform pressure on the order of 25mm Hg. has been found to be both comfortable and render satisfactory results.

DESCRIPTION OF THE PREFERRED EMBODIMENT

Figure 1:
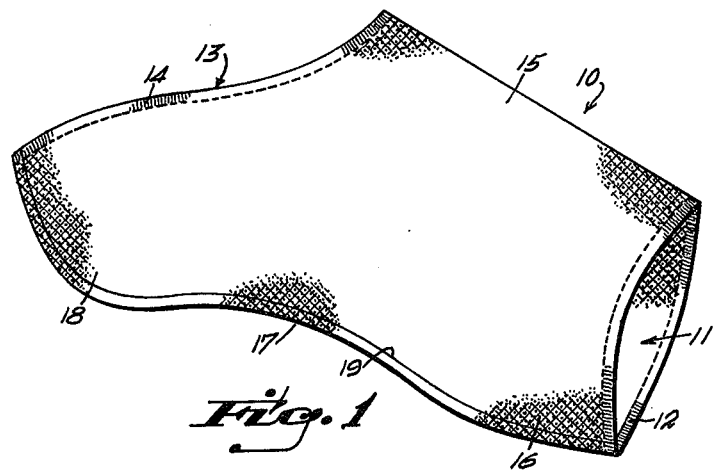
FIG. 1 is an elevational view of the lateral side of a right vein foot support embodying the invention removed from the foot.

Referring in detail to the drawing, 10 generally denotes a vein foot support or foot sock, constructed to embody the invention, which is supplied as a right and left pair but is illustrated herein with respect to the right foot. When not in operative position on the foot, support 10 is seen in FIG. 1 to comprise a modified tubular body having a front toe opening 11 and a top ankle opening 13, both openings being provided with suitable finished edge borders 12 and 14, respectively. The tubular body has a relatively straight configuration extending between openings 11 and 13 along the upper side defining a dorsum portion 15 and an irregular configuration along the bottom side defining a metatarsal enlargement 16, an arch constriction 17 and a heel enlargement 18.

The invention contemplates vein foot support 10 being made of a suitable elastic two-way stretch fabric, that is, a fabric having equivalent elasticity along perpendicular axes, for example, the elastic material used in elastic hosiery and the like, and may be knitted as a unitary sleeve in the well known manner, or may be cut from a sheet of such elastic two-way stretch material to the proper pattern configuration, and as will be clear from FIG. 1, folded along dorsum portion 15 and joined together by an appropriate seam 19 which extends along the bottom between openings 11 and 13.

Seam 19 serving as a joint and borders 12 and 14 serving as a finished edge to avoid tearing or unraveling are formed so as to provide elasticity substantially equivalent to that of the elastic fabric of the body of foot support 10 and not to create any constrictive or binding force.

Figure 2:
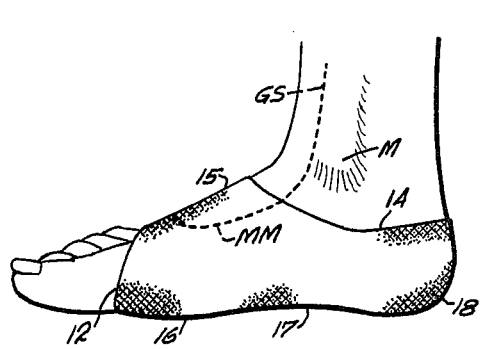
FIG. 2 is a perspective view of the medial side of the right foot showing the vein foot support of FIG. 1 in operative position.
Figure 3:
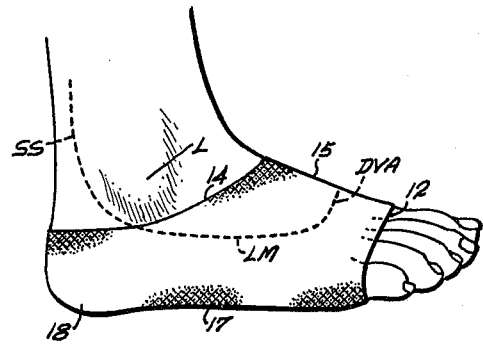
FIG. 3 is a perspective view of the lateral side of the right foot shown in FIG. 2.
Figure 4:
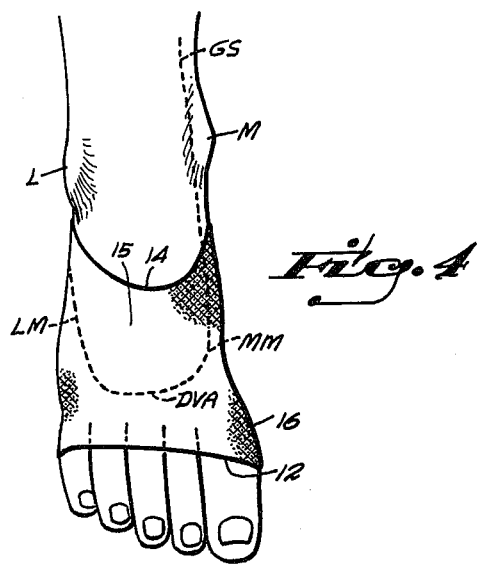
FIG. 4 is a perspective view of the top front of the right foot shown in FIGS. 2 and 3.

Vein foot support 10 is sized and proportioned to the individual foot to exert a compressive, superficial vein supportive, uniform force of pressure of predetermined magnitude upon the metatarsal, tarsal and heel areas of the foot below the ankle. As seen in FIGS. 2, 3 and 4, when in operative, stretched position on the foot, support 10 extends from border 12 of toe opening 11, which surrounds the foot at the base of the toes, rearwardly to encircle the metatarsal area and extend across the dorsum or instep to just below the angle formed by the dorsum and leg when the foot flexes in walking. Support 10 surrounds the tarsal area which includes the arch and heel, completely enclosing the latter and terminates in top border 14 seen to extend above the heel at the lower part of the Achilles tendon and forwardly in a substantially horizontal direction along both sides of the foot passing just below the lateral malleolus L and at the same level and, therefore, spaced below the medial malleolus M, which is seen in FIG. 4 to be located slightly above the lateral malleolus L with respect to a horizontal plane. Top border 14 then curves upwardly across the dorsum not quite reaching the angle as hereinbefore described.

A feature of the invention is the ability of vein foot support 10, due to its particular fit to the foot as hereinbefore described and shown in FIGS. 2, 3 and 4, to exert a uniform pressure on the superficial venous system of the foot including the plantar cutaneous venous network (not shown) located in the fat beneath the heel, the plantar cutaneous venous arch (not shown) in the sole, the dorsal venous arch DVA, the medial marginal vein MM which above border 14 becomes the anteriorly positioned great saphenous vein GS and the lateral marginal vein LM which becomes the posteriorly located small saphenous vein SS. The positioning of border 14 below the lateral malleolus L and medial malleolus M permits the uniform support pressure to be exerted along the medial marginal vein MM and the lateral marginal vein LM thereby correcting the inadequacies found in vein supports which cover these bony protuberances of the ankle, and by reaching just short of the hereinbefore mentioned angle of the ankle, border 14 avoids the wrinkling of the fabric at the ankle, particularly in walking, which has also been found to give rise to an undesirable irregular constriction mainly affecting the medial marginal vein MM.

The foot sock for supporting the superficial veins of the foot herein disclosed is seen to achieve the several objects of the invention and to be well adapted to meet conditions of practical use. As various possible embodiments might be made in this invention, and as various changes might be made in the disclosed structure, it is to be understood that all matter herein set forth and shown in the accompanying drawing are to be interpreted as illustrative and not in a limiting sense.

What is claimed is:

1. A foot sock for supporting the superficial veins of the foot formed of a two-way stretch elastic fabric material comprising a modified tubular body having a front toe opening and a top ankle opening, each with a finished border, said tubular body having a relatively straight configuration extending between said front and top openings along an upper side thereof defining a dorsum portion and an irregular configuration along the bottom side defining a metatarsal enlargement, an arch constriction and a heel enlargement, when in operative position on the foot said toe opening positioning the border thereof along the base of the toes, said top ankle opening being located to position the border thereof to extend above the heel at the lower part of the Achilles tendon and forwardly in a substantially horizontal direction along both sides of the foot passing just below the lateral malleolus and on the opposite side at the same level spaced below the medial malleolus and to curve upwardly across the dorsum just below the angle of the ankle, said dorsum portion cooperating with said metatarsal enlargement, said arch constriction and said heel enlargement to exert a uniform support pressure of a predetermined magnitude on the superficial veins of the metatarsal and tarsal areas of the foot including the medial marginal and lateral marginal veins.

2. The foot sock support defined in claim 1, in which said tubular body is knitted as a unitary seamless structure.

3. The foot sock support defined in claim 1, in which said tubular body is formed from sheet material folded substantially in half and joined in a seam extending along the sole of the foot and the rear of the heel between said openings.

4. The foot sock support defined in claim 1, in which said predetermined magnitude is on the order of 25mm Hg.

* * * * *